(12) United States Patent
Petit et al.

(10) Patent No.: US 7,837,715 B2
(45) Date of Patent: Nov. 23, 2010

(54) CONNECTING ASSEMBLY FOR SPINAL OSTEOSYNTHESIS

(75) Inventors: Dominique Petit, Verton (FR); Stephane Bette, Paris (FR); Muriel Cazin, Bussy-Saint-Georges (FR)

(73) Assignee: Spinevision S.A., Paris (FR)

( * ) Notice: Subject to any disclaimer, the term of this patent is extended or adjusted under 35 U.S.C. 154(b) by 1737 days.

(21) Appl. No.: 10/148,608

(22) PCT Filed: Dec. 1, 2000

(86) PCT No.: PCT/FR00/03365

§ 371 (c)(1),
(2), (4) Date: Sep. 3, 2002

(87) PCT Pub. No.: WO01/39677

PCT Pub. Date: Jun. 7, 2001

(65) Prior Publication Data

US 2003/0045878 A1 Mar. 6, 2003

(30) Foreign Application Priority Data

Dec. 3, 1999 (FR) .................................. 99 15295

(51) Int. Cl.
*A61B 17/70* (2006.01)
(52) U.S. Cl. .................................................. 606/266
(58) Field of Classification Search ............. 606/61, 606/72, 73, 246, 260, 264–267, 269, 270, 606/272, 277–279, 300, 301, 305, 308, 319, 606/320, 328; 403/8, 83, 84, 110; 411/393
See application file for complete search history.

(56) References Cited

U.S. PATENT DOCUMENTS

| | | | | |
|---|---|---|---|---|
| 5,133,717 | A | * | 7/1992 | Chopin ........................ 606/61 |
| 5,254,118 | A | | 10/1993 | Mirkovic |
| 5,352,226 | A | * | 10/1994 | Lin ............................. 606/61 |
| 5,474,551 | A | * | 12/1995 | Finn et al. ..................... 606/61 |
| 5,487,744 | A | * | 1/1996 | Howland ...................... 606/61 |
| 5,562,661 | A | | 10/1996 | Yoshimi et al. |
| 5,575,791 | A | * | 11/1996 | Lin ............................. 606/61 |
| 5,658,284 | A | * | 8/1997 | Sebastian et al. .............. 606/61 |
| 5,741,255 | A | * | 4/1998 | Krag et al. .................... 606/61 |
| 5,879,351 | A | * | 3/1999 | Viart ........................... 606/61 |
| 5,947,967 | A | * | 9/1999 | Barker ......................... 606/61 |
| 6,030,388 | A | * | 2/2000 | Yoshimi et al. ............. 606/278 |
| 6,146,383 | A | * | 11/2000 | Studer ......................... 606/61 |
| 6,187,005 | B1 | * | 2/2001 | Brace et al. ................... 606/61 |
| 6,280,443 | B1 | * | 8/2001 | Gu et al. ...................... 606/61 |

(Continued)

FOREIGN PATENT DOCUMENTS

DE 92 15 561 1/1993

(Continued)

*Primary Examiner*—Todd E Manahan
*Assistant Examiner*—David Comstock
(74) *Attorney, Agent, or Firm*—Bachman & LaPointe, P.C.

(57) ABSTRACT

A connecting assembly for spinal osteosynthesis has a bone anchoring element including a connection zone designed to co-operate with a connecting device. The connecting device comprises in its lower part a spherical shape designed to enable the connecting device to be freely positioned in a connector or in a linking element having a cavity with matching shape, the spherical shape forming a stop element for longitudinal positioning with the connector or with the linking element.

20 Claims, 16 Drawing Sheets

U.S. PATENT DOCUMENTS 6,328,739 B1 * 12/2001 Liu et al. .................. 606/61
6,676,661 B1 * 1/2004 Benlloch et al. ........... 606/61
6,749,613 B1 * 6/2004 Conchy et al. ............. 606/61

FOREIGN PATENT DOCUMENTS

| | | | |
|---|---|---|---|
| FR | 2 789 886 A1 * | 2/1999 | |
| FR | 2 796 546 A1 * | 7/1999 | |
| FR | 2 776 500 | 10/1999 | |
| FR | 2776500 A1 * | 10/1999 | |

* cited by examiner

CONNECTING ASSEMBLY FOR SPINAL OSTEOSYNTHESIS

BACKGROUND OF THE INVENTION

The objective of the present invention is an application in the field of spinal osteosynthesis.

The present invention relates more particularly to a connecting assembly for spinal osteosynthesis comprising a bone anchor means and a connecting zone intended to collaborate with a connecting means.

The prior art knows connecting assemblies, particularly German Utility Model Number 92 15 561.

The major disadvantage with the connecting assemblies of the prior art lies in the fact that they offer only little in the way of possibilities for relative movement of the various elements.

SUMMARY OF THE INVENTION

The present invention relates, in its broadest sense, to a connecting assembly as claimed in claim 1.

The connecting assembly according to the invention is characterized in that the connecting means comprises, in its lower part, a spherical shape to allow the connecting means to be positioned freely in a connector or in a linking element having a cavity of complementary shape, this spherical shape forming an end stop for longitudinal positioning with the connector or with the linking element.

Advantageously, the connecting means is crimped into the connector in such a way as to secure the two parts together while leaving the connecting means free to rotate in the connector.

According to an alternative form, the connector has an entry cone in the connector for the passage of the ancillary for turning the connecting means.

As a preference, the angular excursion of the connector on the connecting means is about 30 degrees when the ancillary for turning the connecting means is in place.

According to a preferred embodiment, the connecting means has slots machined in the spherical part of the connecting means so as to create deformation when the system is definitively tightened. Said slots are preferably longitudinal.

Said connecting means also preferably comprises a skirt in its lower part. This skirt is threaded on its lower end to make it easier for it to penetrate bone.

The bone anchor means preferably comprises, in its upper part, a part for pre-guiding said connecting means so as to allow good alignment between the connecting means and the screw.

The connecting means may consist of a nut.

The connector is provided with at least one location for accommodating a linking element.

The connector may comprise a locking location opening into the cavity forming the housing of the spherical shape and into the location accommodating the linking element.

The connecting assembly according to the invention may comprise a locking cylinder which can be introduced into said locking location. This locking cylinder can be replaced by a linking element.

The locking location may furthermore also open in a roughly perpendicular direction for the introduction of a locking plug. The locking plug may comprise a stub intended to collaborate with a location formed in said locking adjusting cylinder.

The location for accommodating a linking element may be of oblong shape in the case of a connector of closed type, or in the shape of a "U" open on one of the faces in the case of a connector of open type.

The connector may be provided with two locations for accommodating a linking element formed of a bent rod forming a U closed at its ends and in that the linking element has a cavity of a shape that complements the spherical shape.

A threaded part, in the shape of a hexagon, is preferably formed at the upper end of the connecting means, so as to allow a secondary nut to be screwed on.

BRIEF DESCRIPTION OF THE DRAWINGS

The present invention will be better understood from reading the description of a nonlimiting exemplary embodiment which follows, referring to the appended drawings in which.

DETAILED DESCRIPTION OF THE PREFERRED EMBODIMENT(S)

Figure 1:
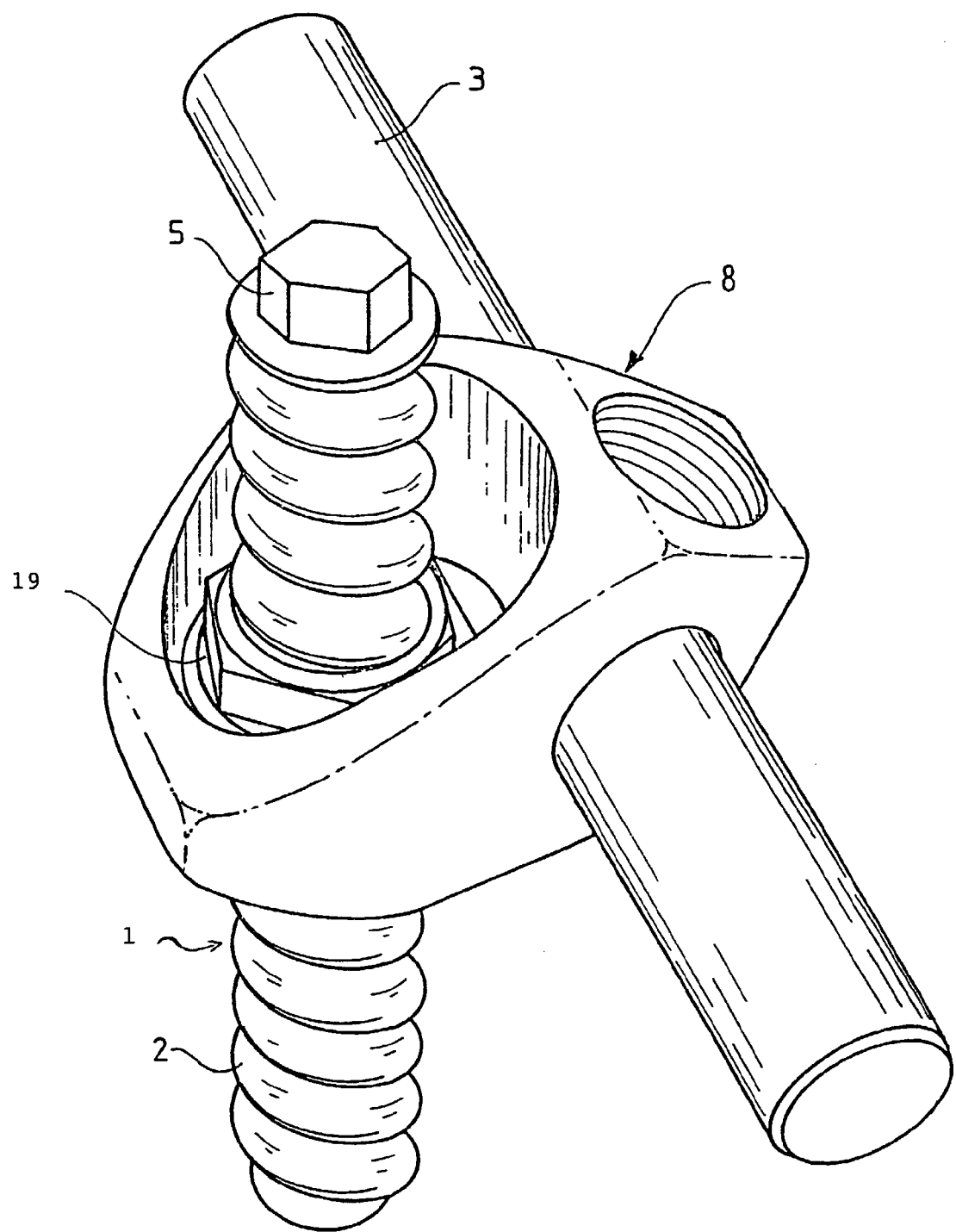
FIG. 1 depicts a perspective view of a connecting assembly in its basic version with a screw bone anchor means.

The present invention relates to a connecting assembly, illustrated in its basic version in FIG. 1, for spinal osteosynthesis comprising a bone anchor means comprising a connecting zone (29) intended to collaborate with a connecting means.

The bone anchor means may consist of a screw (1) comprising at least one bone screw thread (2).

The screw (1) further comprises a connecting zone (29) intended to collaborate with said connecting means.

The screw thread of bone type (2) has one main function: that of anchoring into bone. It may possibly have a secondary function: that of accommodating the connecting system for a linking element when the connecting zone (29) is coincident with the upper part of the bone screw thread (2).

A system (5) for turning is provided on the upper end of the screw (1). This system, for example a hexagon, has two functions: that of allowing the screw (1) to be turned as it penetrates the bone, and also a role of locking rotation during final tightening of the mechanism so as to prevent the screw (1) from penetrating any further into the bone.

The connecting means makes it possible to produce a longitudinal end stop along the screw (1) either directly for the linking element (3') when, for example, the latter is a bent rod forming a U closed at its ends, or via a connector (8).

The connecting means may consist of a nut (19). In this case, in which the tapped thread (7) of the nut (19) corresponds to the screw thread of the connecting zone (29); that is to say, in the version illustrated in FIGS. 1, 2 and 3, to the bone screw thread (2) of the screw (1). The nut (19) is screwed onto the part of the screw which is not buried in the bone.

The nut (19) is of spherical shape (20) in its lower part. This spherical shape is intended to allow the nut (19) to be positioned freely on the connector (8) where there is a housing of the same type, or on the linking element (3). This spherical shape (20) also serves as an end stop for longitudinal positioning with the connector (8) or with the linking element (3). In the preferred application, the connecting means is crimped into the connector (8) or into the linking element (3) so as to secure the two parts together while leaving the connecting means free to rotate on the connector (8) or on the linking element (3).

Figure 3:
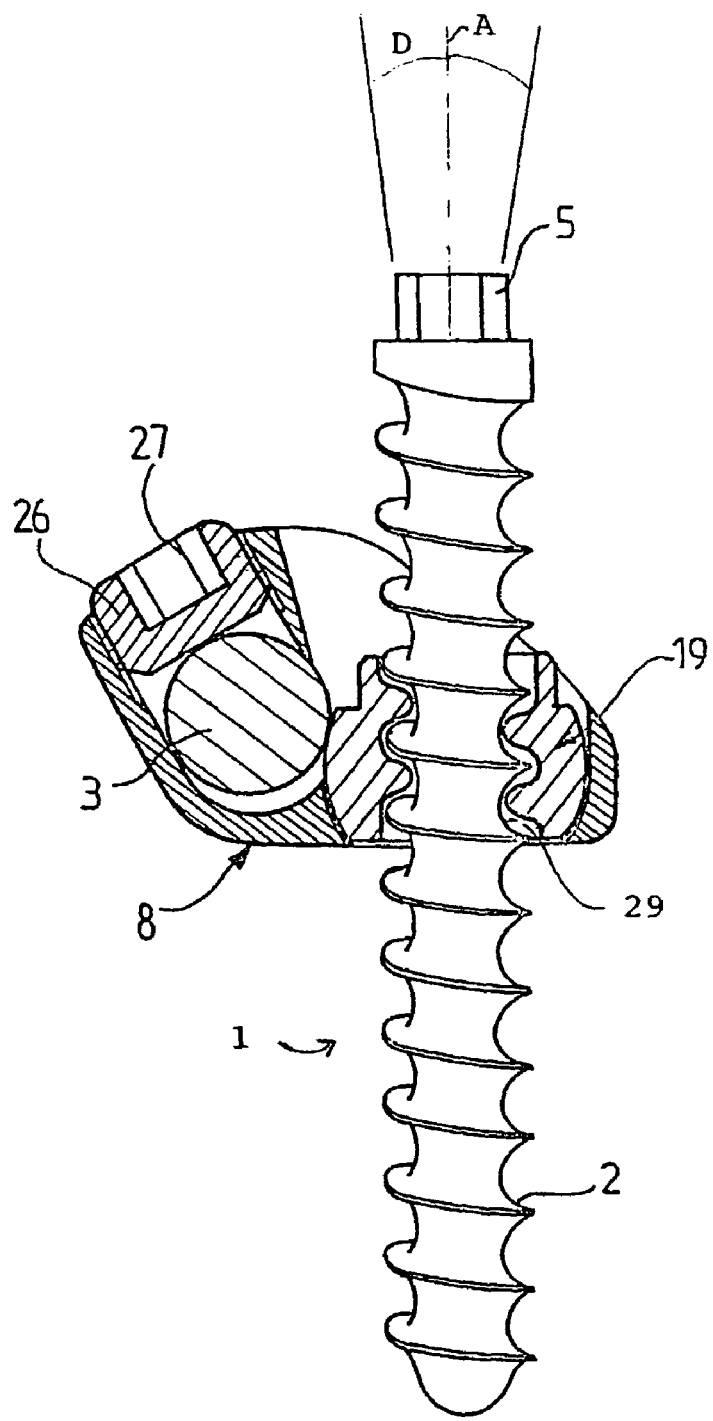
FIG. 3 depicts a view in part section of the connecting assembly of FIG. 1.

A drive system (21), for example an external hexagon, is also provided on the connecting means above its spherical part (20) so as to allow its height to be adjusted together with that of the connector (8) or of the linking element (3') along the screw (1). Because of the possibility of the connector turning on the connecting means, an entry cone (22) in the connector (8) is provided for the passage of the ancillary for turning the connecting means. By way of example, the angular excursion D of the axis A of the connector on the connecting means is, in the preferred application, 30 degrees when the ancillary for turning the connecting means is in place, as illustrated in FIG. 3.

Slots (23) are machined in the spherical part of the connecting means so as to create a deformation when the system is definitively tightened. The purpose of this deformation is to lock the rotation of the screw (1).

Figure 2:
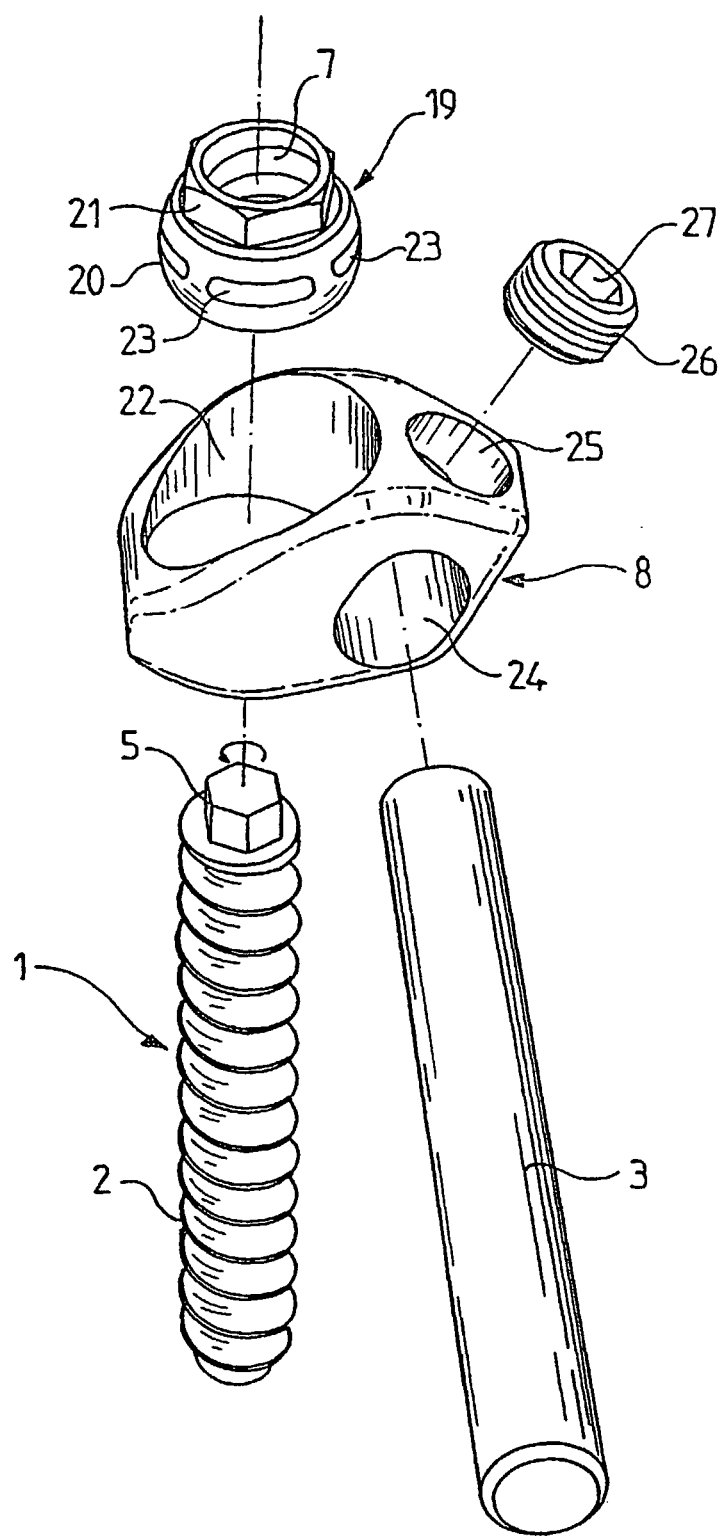
FIG. 2 depicts an exploded view of the connecting assembly of FIG. 1.
Figure 4:
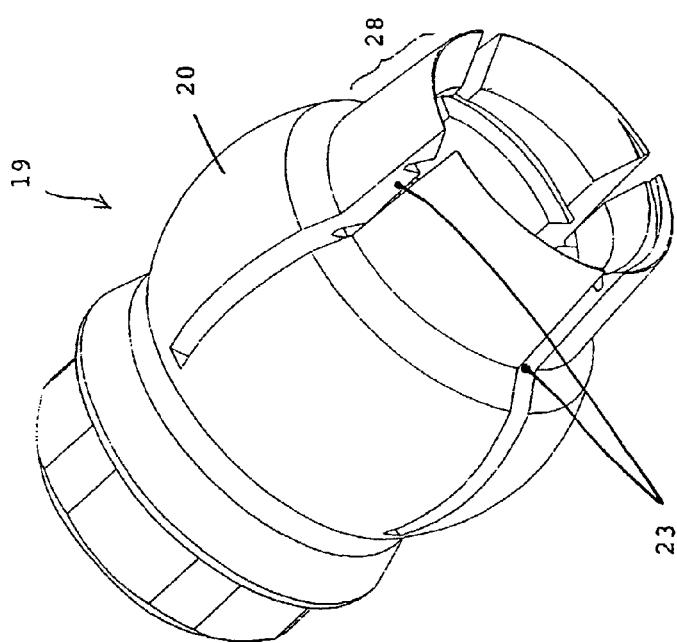
FIG. 4 depicts a perspective view of a nut according to the invention with a skirt and longitudinal slots.

The slots (23) may be positioned transversely, as illustrated in FIG. 2, or longitudinally, as illustrated in FIG. 4.

The longitudinal slots are preferably open in the lower part of the spherical shape (20). There may be one, two, three, four, five or more of these.

Figure 5:
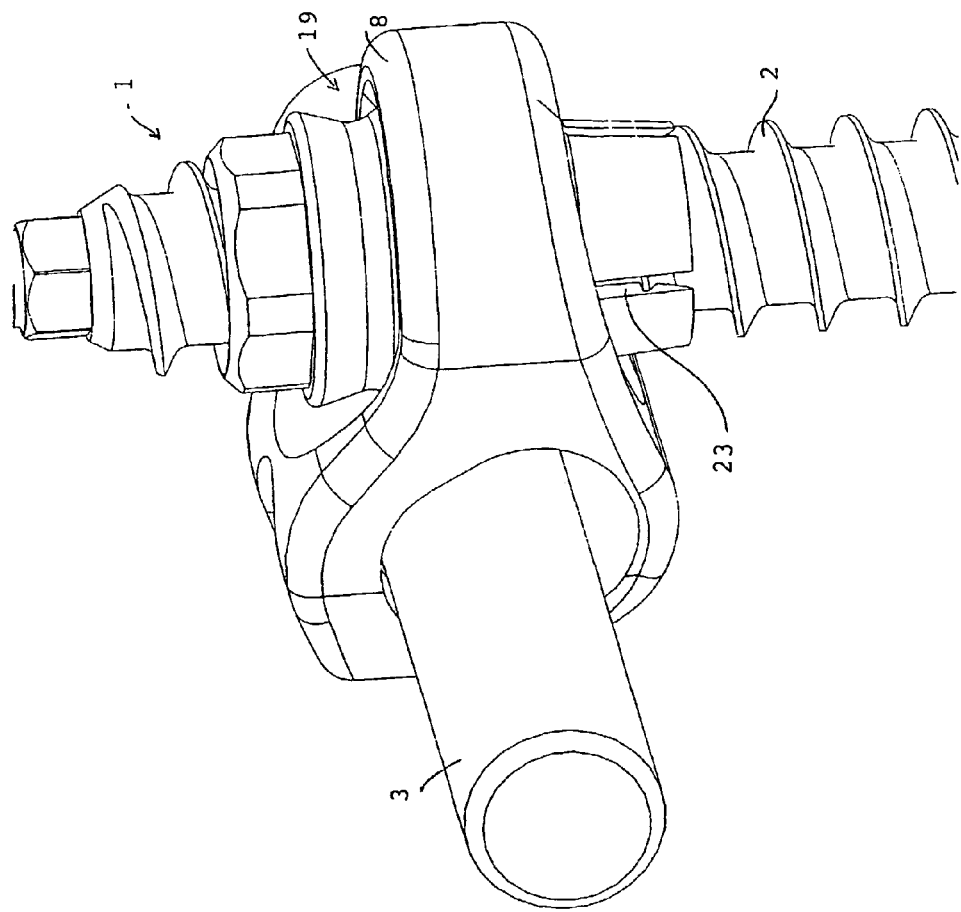
FIG. 5 depicts a part view in perspective of a nut according to FIG. 4 mounted on a connector.

The connecting means in its lower part comprises a skirt (28) also visible in FIG. 4, and in FIG. 5. This skirt (28) makes it possible to have a mechanical transition between the screw (1) and the spherical shape (20). The issue here is that too abrupt a transition would encourage the screw to break at the base of the spherical shape (20) under dynamic loading. The skirt (28) thus allows a better distribution of the stress of the screw working its way into the nut.

This skirt (28) may be threaded on its end to make it easier to penetrate bone.

Figure 6:
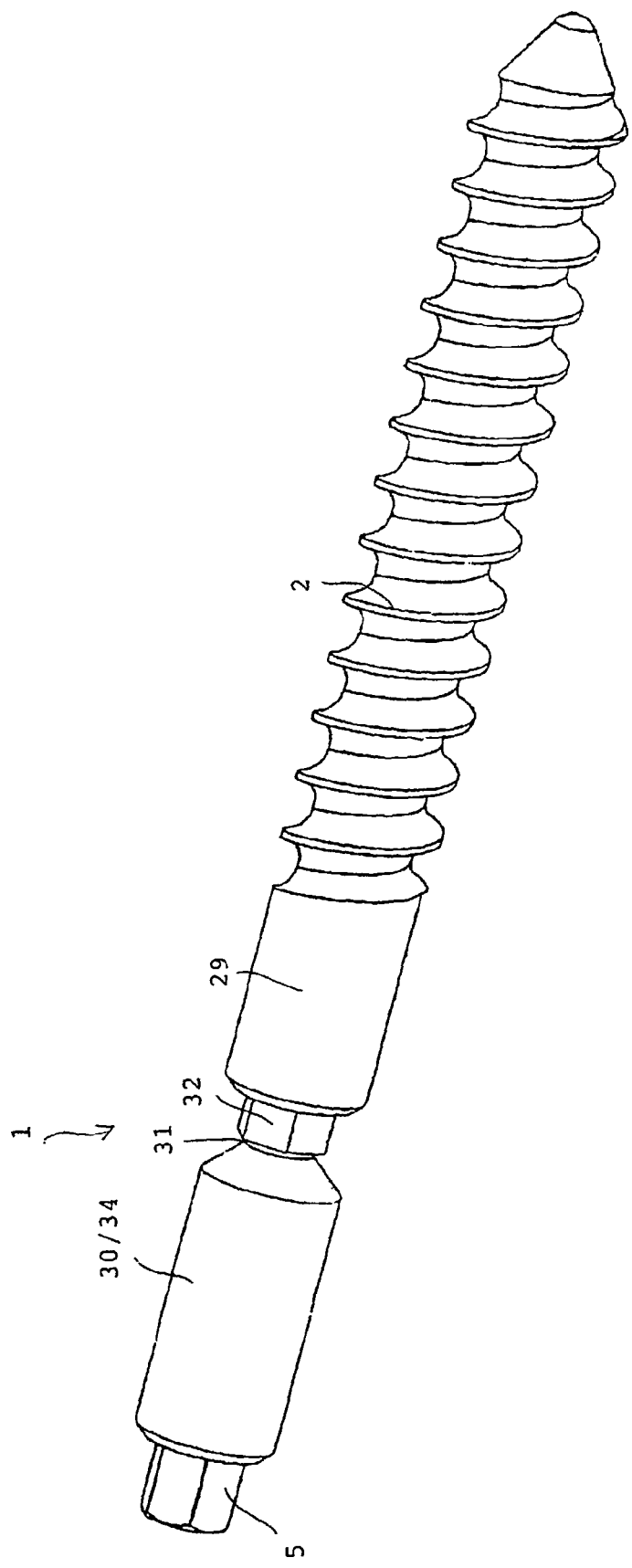
FIG. 6 depicts a perspective view of a screw comprising a pre-guiding part and/or a return part that is plain, and a plain connecting part.
Figure 7:
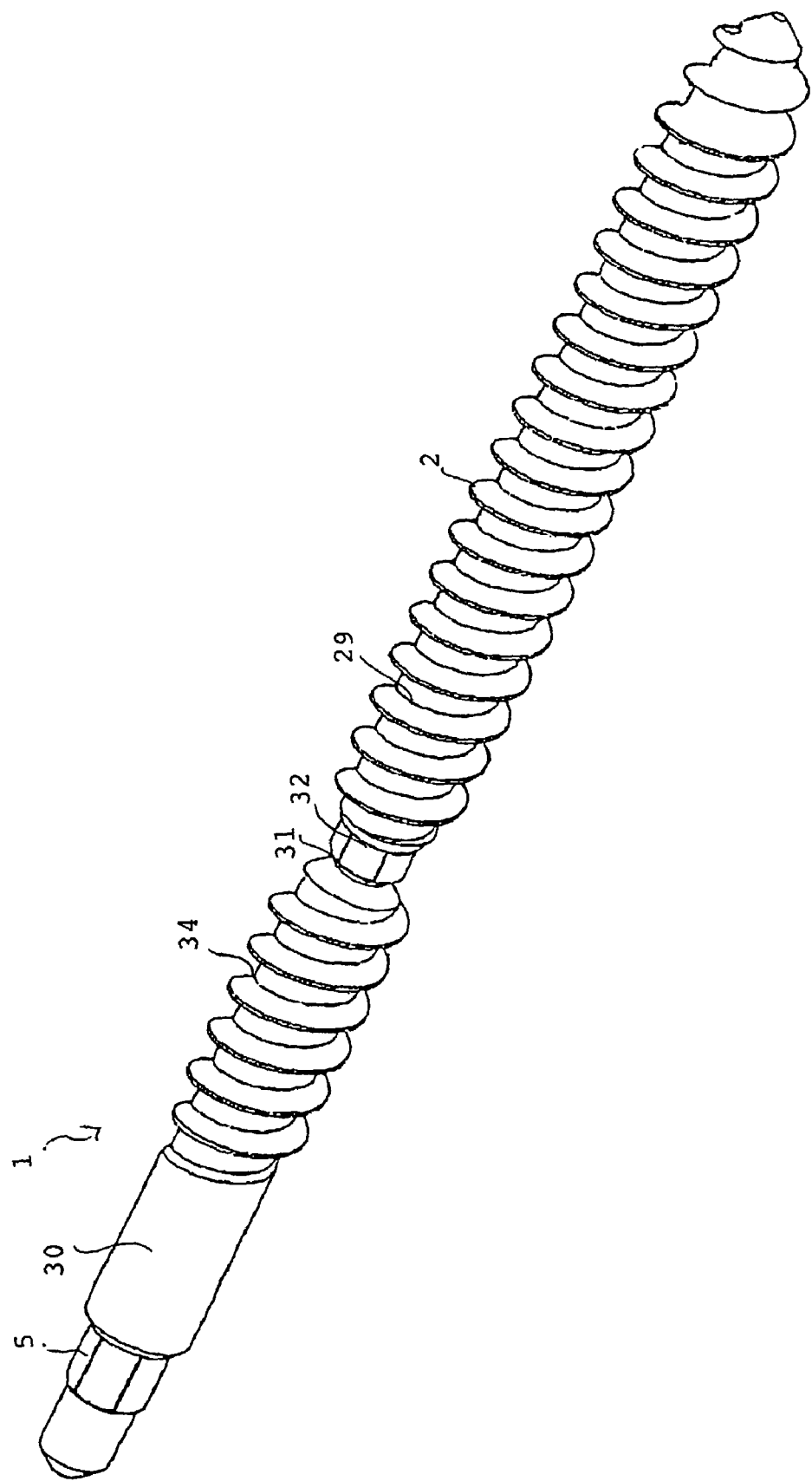
FIG. 7 depicts a perspective view of a screw comprising a plain pre-guiding part, a threaded return part and a threaded connecting part coincident with the bone screw thread.
Figure 8:
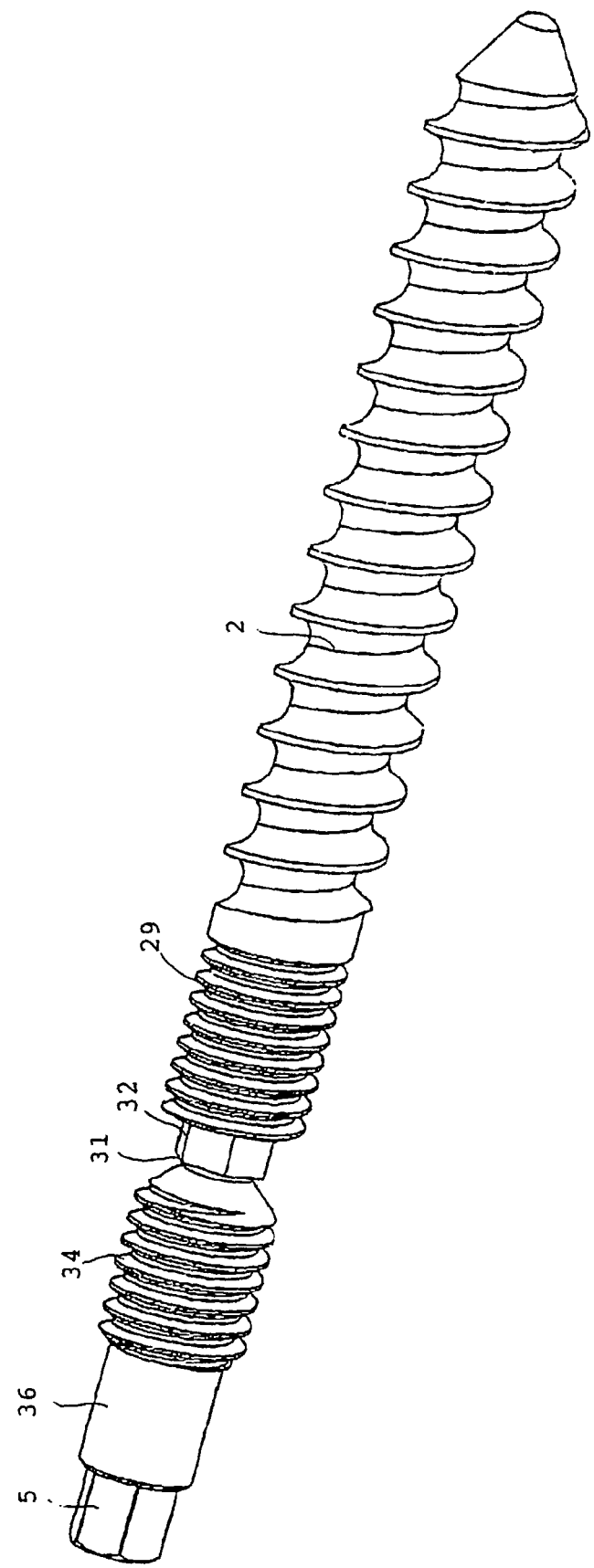
FIG. 8 depicts a perspective view of a screw comprising a plain pre-guiding part, a threaded return part and a threaded connecting part not coincident with the bone screw thread.
Figure 9:
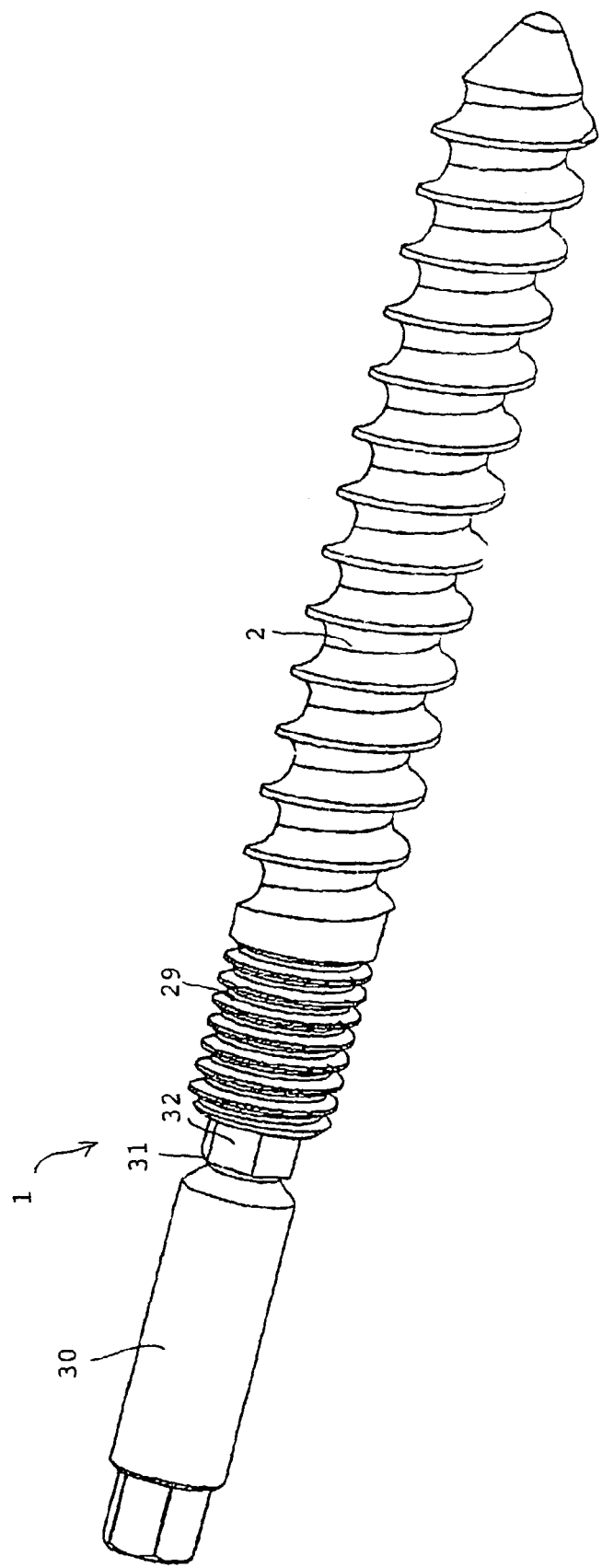
FIG. 9 depicts a perspective view of a screw comprising a plain pre-guiding part and a threaded connecting part not coincident with the bone screw thread.

The connecting zone (29) of the screw (1) may be formed in the upper part of the bone screw thread and may have a screw thread identical to the bone screw thread as illustrated in FIG. 7, but it may just as easily have a different screw thread as illustrated in FIGS. 8 and 9, or alternatively not be threaded, as illustrated in FIG. 6.

In the latter incidence, the connecting means therefore has a plain interior wall and does not constitute a nut.

In an alternative form, the screw (1) comprises, in its upper part, a plain pre-guiding part (30) so as to ensure correct alignment of the connecting means as the connecting means is put in place, especially when it is a nut (19).

This pre-guiding part (30) has plain walls, as illustrated in FIGS. 6 to 9. Its outside diameter is roughly equivalent to that of the inside diameter of the connecting means so as to ensure the most linear possible longitudinal guidance (without angular slope).

The plain pre-guiding part (30) may also act as a return zone (34) when spondylolisthesis is being treated.

This return zone (34) may also be threaded with a screw thread identical to the bone screw thread (2), as illustrated in FIG. 7, or with a different screw thread, as illustrated in FIG. 8.

The screw (1) may also be equipped with a slot (31) making it easier for the screw (1) comprising the plain pre-guiding part (30) and/or the return zone (34) to be detached from the top. Machined under this circular slot (31) is a drive system (32) which, after breakage, becomes the system for driving the screw (1), particularly for the ablation of the connecting assembly, as illustrated in FIGS. 7 to 9.

In the basic version, the connector (8) is provided with just one location for accommodating a linking element (3) formed by a rod. This location may be of oblong shape (24) in the case of a connector (8) of closed type, or in the shape of a "U" open on one of the faces in the case of a connector of open type. In the case of a connector (8) of closed type, the rod needs to be threaded into it, while in the case of an open connector, the rod (3) can be introduced over the connector from the rear or from the side.

The location (24) for accommodating the rod (3) is provided in such a way that the rod (3) can bear against the spherical shape (20) of the nut (19), as illustrated in FIG. 3.

It is therefore understood that the rod (3) with respect to the screw (1) is free in three axes of rotation and in two directions of translation:

rotation of the connector (8) and therefore of the rod (3) about the fixing means in two axes perpendicular to the screw (1);

rotation of the connector (8) and therefore of the rod (3) about the fixing means in an axis identical to that of the screw (1);

translation of the rod (3) in the connector (8) along the axis of this rod;

translation of the connector (8) and therefore of the rod (3) along the screw (1) by virtue of the possibility of adjusting the fixing means.

Furthermore, the turning of the rod (3) on itself may offer the connecting assembly an additional degree of freedom.

The connector (8) also has a locking location (25) for accommodating a locking system. In the basic application, this locking system is a nut (26) provided with a drive system (27) for applying sufficient torque for the mechanical integrity of the assembly, as illustrated in FIG. 3.

Such a connection is locked by the pressure of the linking element (3) on the spherical shape (20). As the linking element (3) is secured to the connector (8) by the pressure applied by the nut (26), the degrees of freedom are therefore all fixed.

Figure 10:
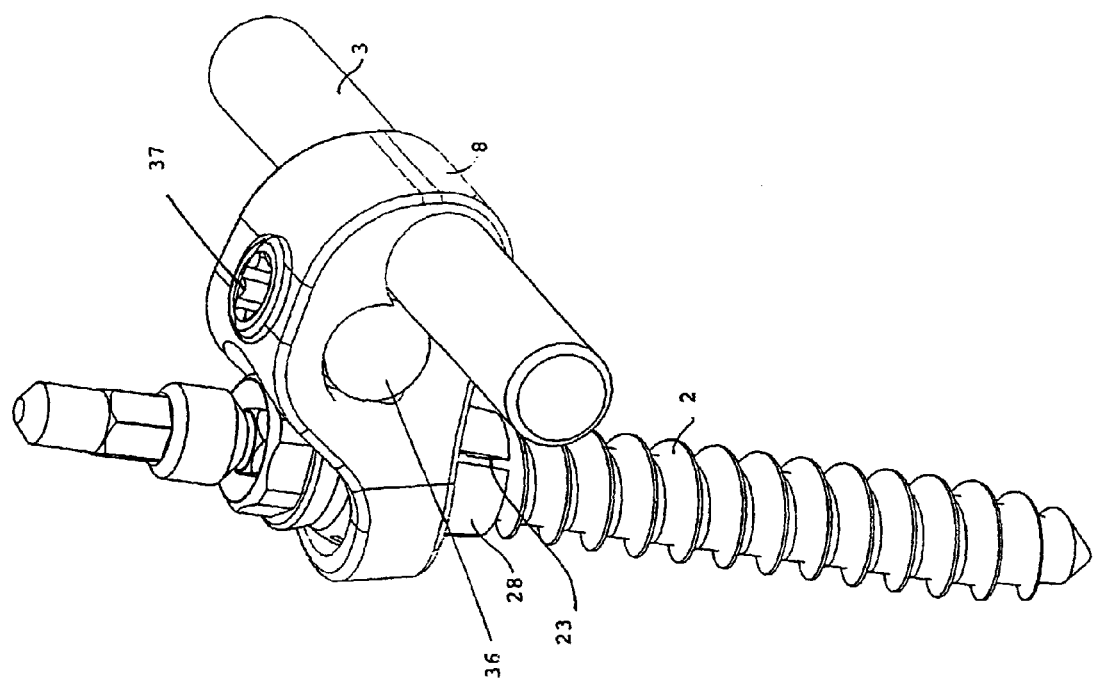
FIG. 10 depicts a perspective view of a connecting assembly with a system of locking the connecting means and the connecting rod together.

In an alternative form, said connector (8) comprises an evolved locking location (25), into which a locking cylinder (36) can be introduced, said locking location (25) also opening in a roughly perpendicular direction for the insertion of a locking plug (37), as illustrated in FIG. 10.

Figure 11:
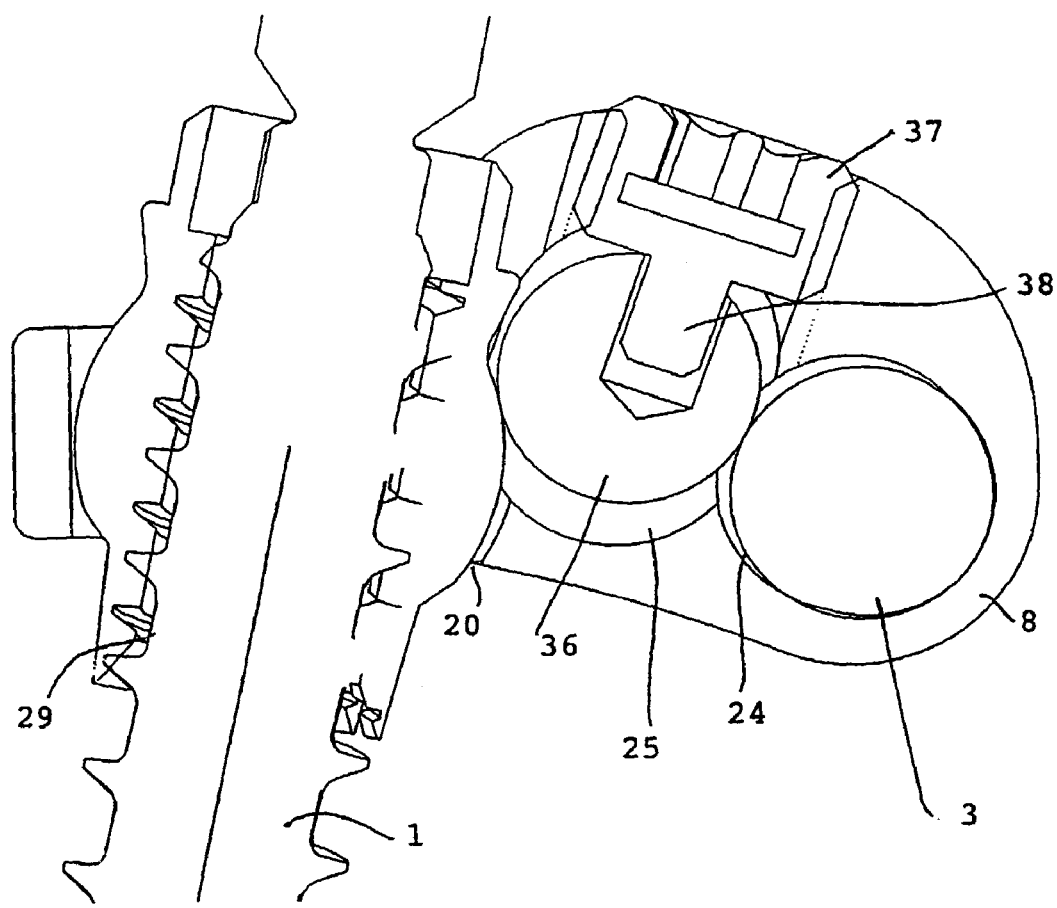
FIG. 11 depicts a sectional view of the connecting assembly of FIG. 10 with a locking cylinder.

Furthermore, said locking plug (37) comprises a stub (38) intended to collaborate with a location formed in said locking cylinder (36) so as to prevent the locking cylinder (36) from becoming detached from the connector when the assembly is not yet tightened up, as illustrated in FIG. 11.

Figure 12:
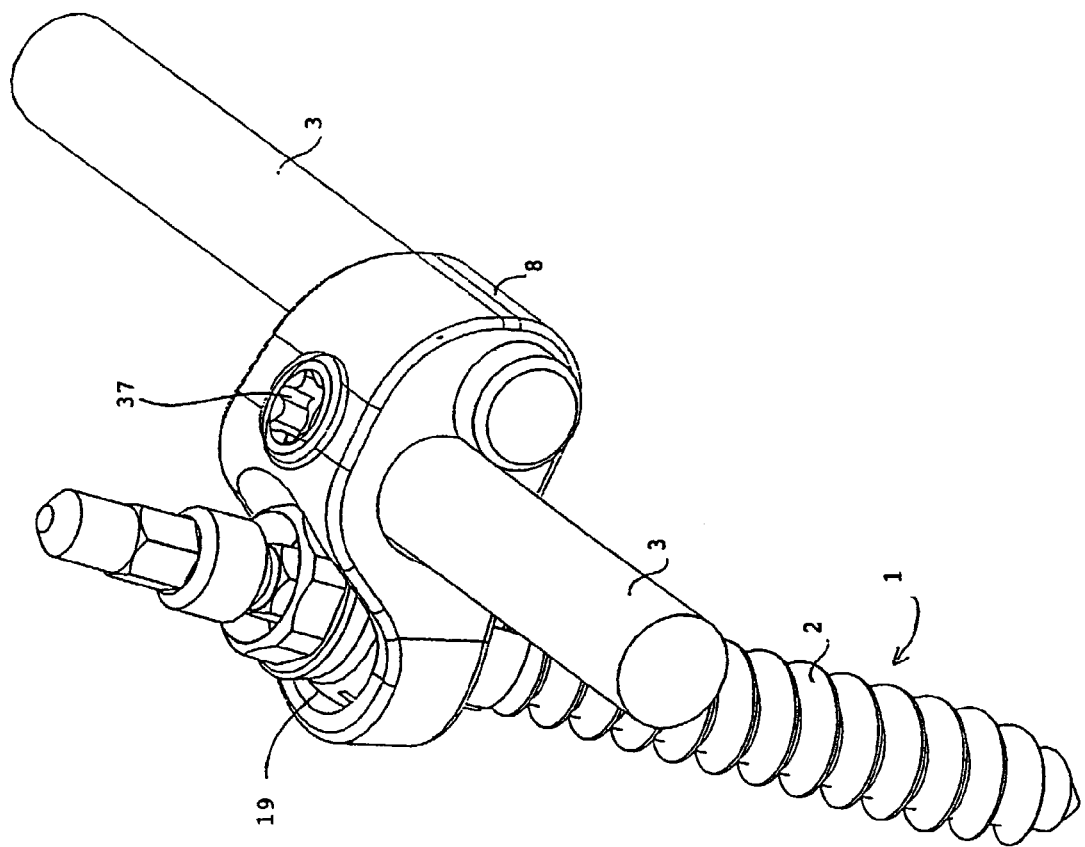
FIG. 12 depicts a perspective view of the connecting assembly of FIG. 10 with a second connecting element.

The locking cylinder (36) can be replaced by a linking element (3) so as to obtain an additional possibility of connection, as illustrated in FIG. 12.

In this version, the assembly is tightened up by the force applied both to the linking element (3) and to the spherical part (20) by the connecting cylinder (36) or by the second linking element (3).

It is necessary to provide a number of connectors so as to be able to choose the one whose distance between the screw and the linking element or the linking elements is appropriate.

Figure 13:
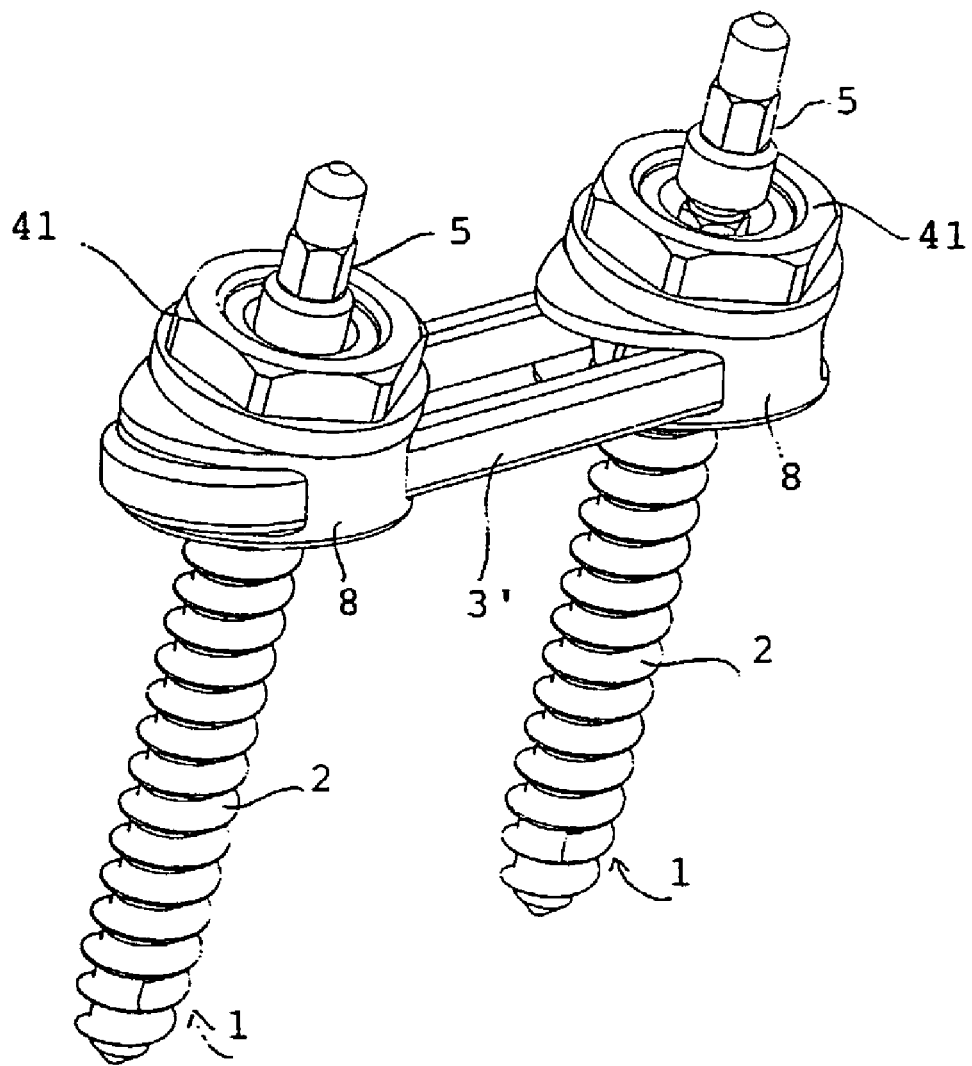
FIG. 13 depicts a perspective view of connecting assembly in an alternative form with a bent connecting rod forming a U closed at its ends.

In another version, the connector (8) is provided with two locations for accommodating a linking element (3') formed of a bent rod forming a U closed at its ends, as illustrated in FIG. 13, and the linking element (3') has a cavity of a shape that complements the spherical shape (20).

The rod is bent on itself, so as to form a ring of oblong cross section likeable to a plate in the field of osteosynthesis.

Figure 14:
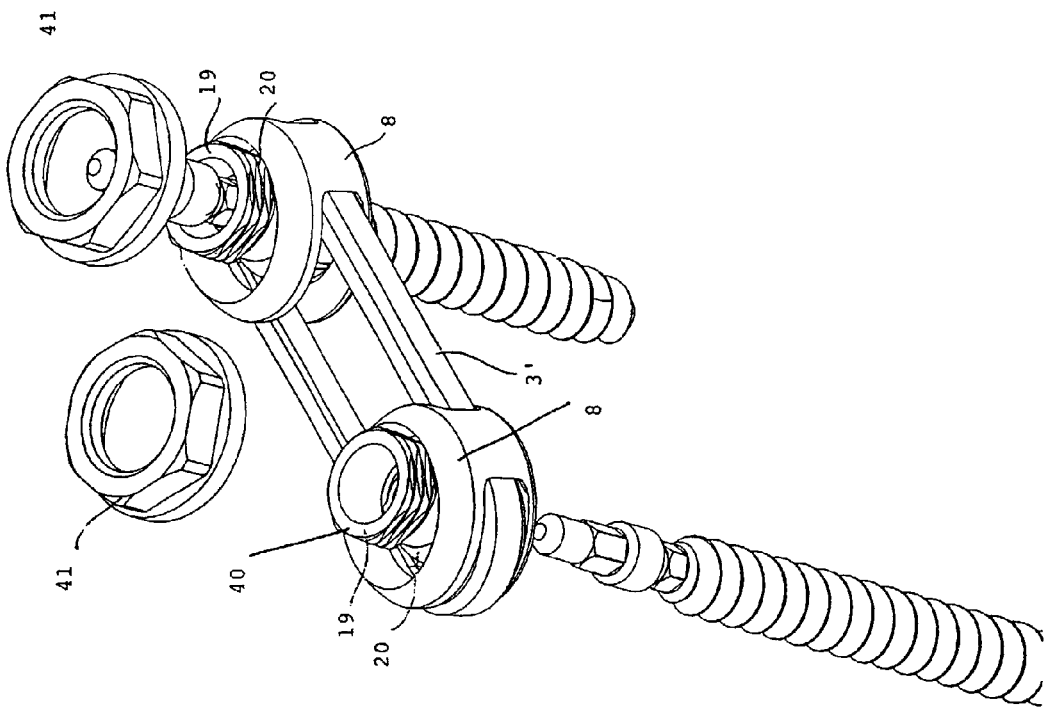
FIG. 14 depicts an exploded view of the connecting assembly of FIG. 13.

A threaded part (40), in the shape of a hexagon, is formed at the upper end of the nut (19), as illustrated in FIG. 14, so as to allow a secondary nut (41) to be screwed on and the assembly to be tightened.

The connector (8) is likeable to a washer having a cavity for the passage of the linking element.

Figure 15:
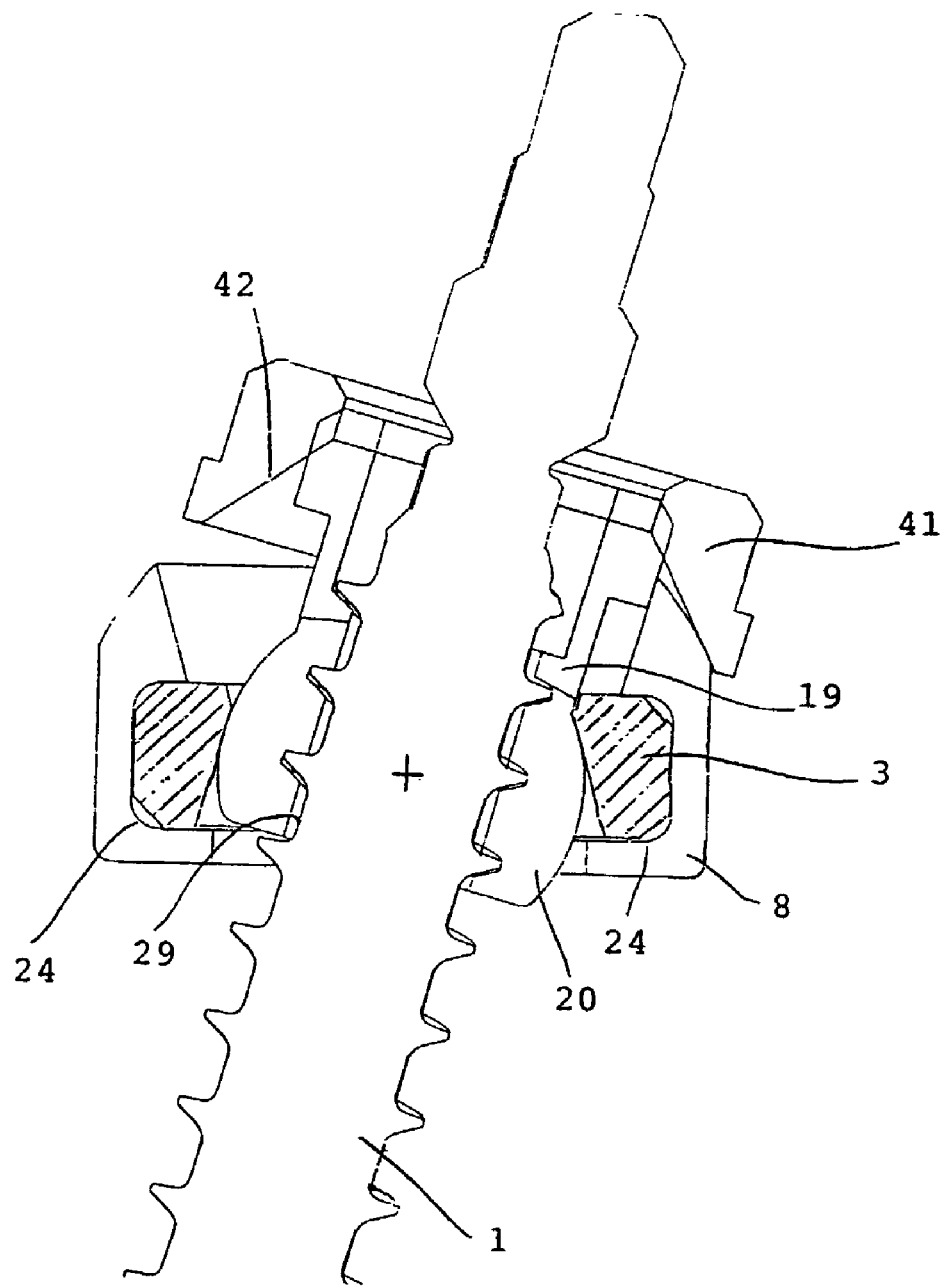
FIG. 15 depicts a section part view of the connecting assembly of FIG. 13.

A chamfer (42), illustrated in FIG. 15, is formed on the secondary nut (41); this chamfer is intended to collaborate with the outer upper part of the connector (8).

In this version, the fixing means is crimped onto the connector (8), trapping the linking element (3'), so as to secure the three parts together while at the same time allowing the fixing means to turn in the connector (8) and allowing translational movement of the linking element (3') in this connector (8).

Final tightening is performed by screwing the secondary nut (41) onto the fixing means so as to fix all the degrees of freedom.

Figure 16:
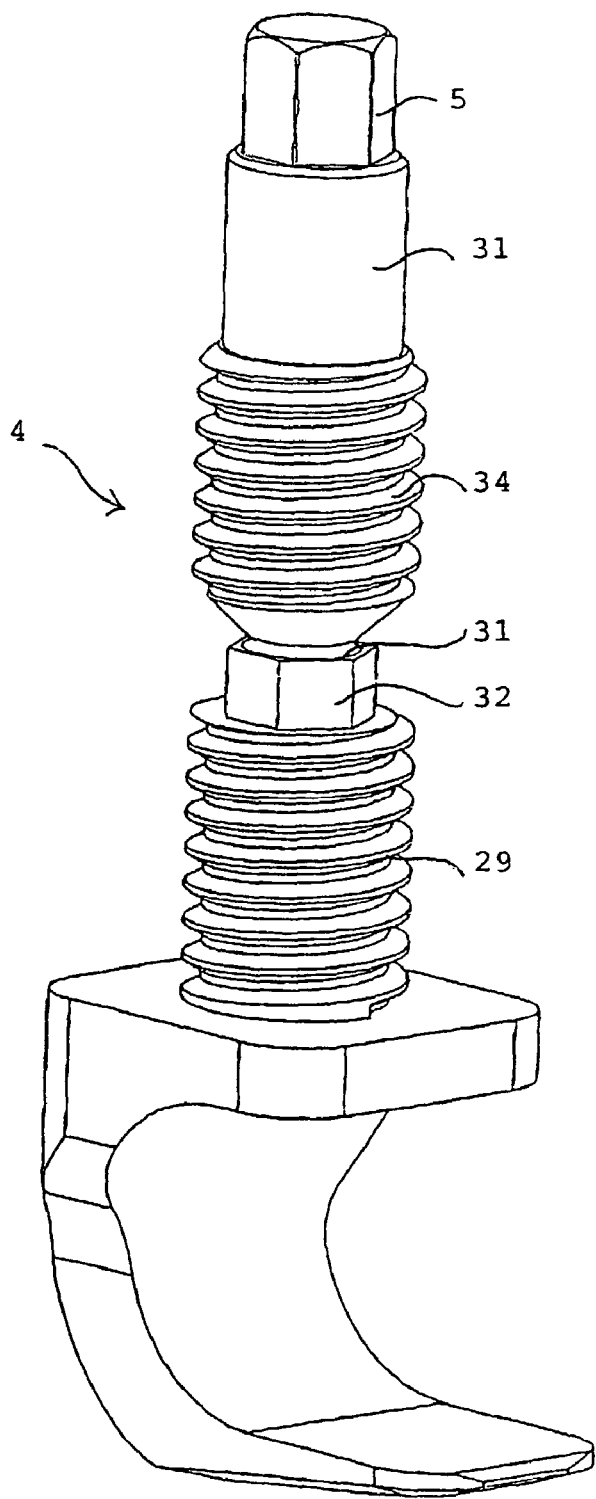
FIG. 16 depicts a perspective view of a hook bone anchor means.
Figure 17:
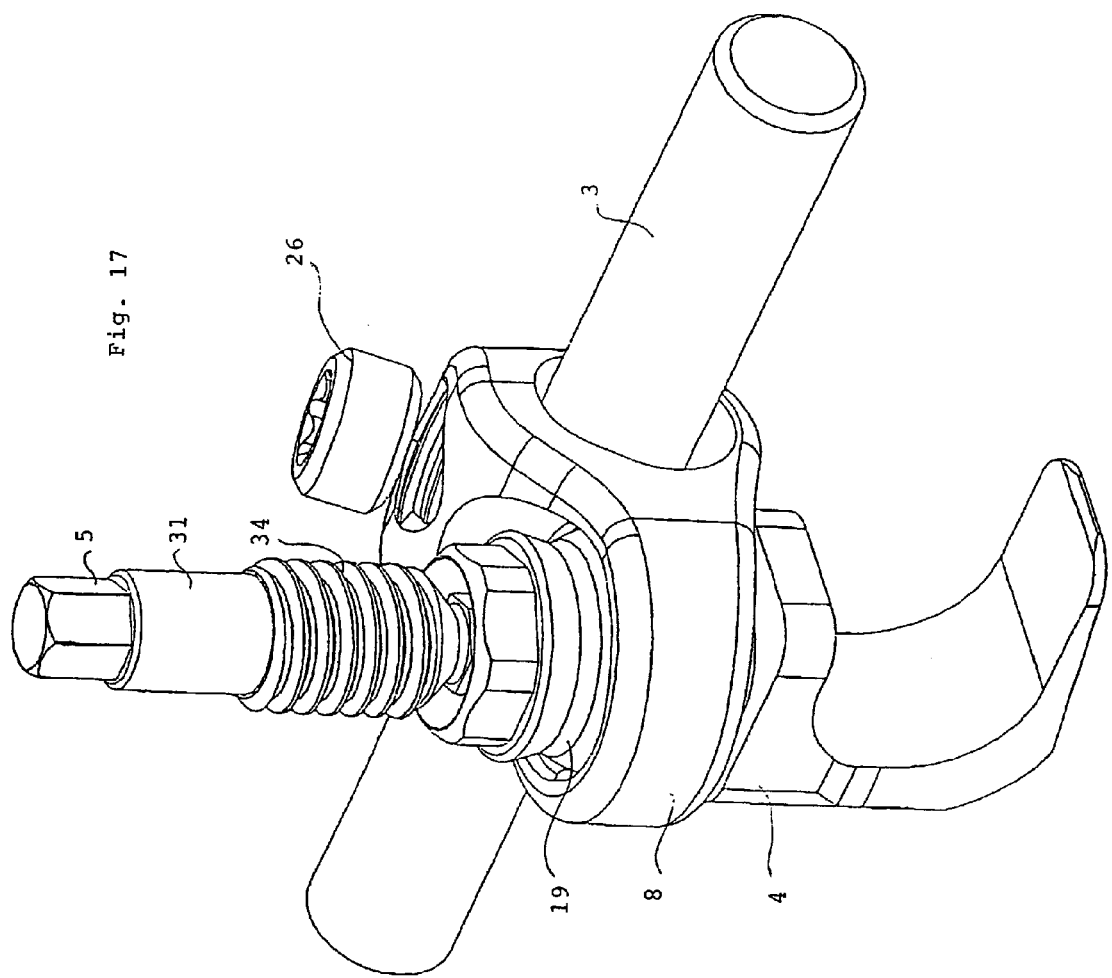
FIG. 17 depicts a perspective view of a connecting assembly with a hook bone anchor means.

The bone anchor means may just as easily consist of a hook (4), as illustrated in FIGS. 16 and 17.

The invention claimed is:

1. A connecting assembly for spinal osteosynthesis comprising:
   a bone anchor means having a connecting zone which collaborates with a connecting means,
   said bone anchor means having an external thread which engages a threaded portion of said connecting means,
   a connector having a cavity forming the housing of said connecting means and at least one location for accommodating a linking element or a locking cylinder,
   said at least one location opening into the cavity forming the housing of said connecting means,
   said connecting means comprising, in its lower part, a spherical shape part for allowing the connecting means to be positioned freely in at least one of the connector or the linking element having a cavity of complementary shape and, when the connecting means are positioned in the cavity of complementary shape of the connector or the linking element, for allowing the connector and the linking element to rotate around the connecting means in three axes,
   said linking element or said locking cylinder contacting said spherical shape part of said connecting means and pressing against said connecting means, and
   said spherical shape part forming an end stop for longitudinal positioning with said at least one of the connector and the linking element.

2. The connecting assembly for spinal osteosynthesis as claimed in claim 1, further comprising the connecting means being crimped into the connector while leaving the connecting means free to turn in the connector.

3. The connecting assembly for spinal osteosynthesis as claimed in claim 1, further comprising the connector having an entry cone for the passage of an ancillary for turning the connecting means.

4. The connecting assembly for spinal osteosynthesis as claimed in claim 3, further comprising an angular excursion of the connector on the connecting means being about 30 degrees when the ancillary for turning the connecting means is in place.

5. The connecting assembly for spinal osteosynthesis as claimed in claim 1, further comprising the connecting means having slots machined in the spherical shaped part so as to create deformation when the assembly is definitively tightened.

6. The connecting assembly for spinal osteosynthesis as claimed in claim 5, further comprising said slots being longitudinal slots.

7. The connecting assembly for spinal osteosynthesis as claimed in claim 1, further comprising said connecting means having a skirt in its lower part.

8. The connecting assembly for spinal osteosynthesis as claimed in claim 7, wherein said skirt is threaded on its lower end to make it easier for said skirt to penetrate bone.

9. The connecting assembly for spinal osteosynthesis as claimed in claim 1, wherein the bone anchor means comprises, in its upper part, a plain part for pre-guiding said connecting means.

10. The connecting assembly for spinal osteosynthesis as claimed in claim 1, wherein the connecting means consists of a nut.

11. The connecting assembly for spinal osteosynthesis as claimed in claim 1, wherein the connector is provided with at least one location for accommodating said linking element.

12. The connecting assembly for spinal osteosynthesis as claimed in claim 1, wherein said connector has a locking location opening into a cavity forming a housing of the spherical shape part and into a location accommodating the linking element.

13. The connecting assembly for spinal osteosynthesis as claimed in claim 12, further comprising a locking cylinder to be introduced into said locking location.

14. The connecting assembly for spinal osteosynthesis as claimed in claim 13, wherein said locking cylinder can be replaced by a linking element.

15. The connecting assembly for spinal osteosynthesis as claimed in claim 13, wherein said locking location also opens in a roughly perpendicular direction for the introduction of a locking plug.

16. The connecting assembly for spinal osteosynthesis as claimed in claim 15, wherein said locking plug comprises a stub for collaborating with a location formed in said locking cylinder.

17. The connecting assembly for spinal osteosynthesis as claimed in claim 1, wherein each said at least one location is of an oblong shape and said connector is of a closed type.

18. The connecting assembly for spinal osteosynthesis as claimed in claim 1, wherein a threaded part in the shape of a hexagon is formed at an upper end of the connecting means so as to allow a secondary nut to be screwed on.

19. A connecting assembly for spinal osteosynthesis comprising:
- a bone anchor means having a connecting zone which collaborates with a connecting means,
- said bone anchor means having an external thread which engages a threaded portion of said connecting means,
- a connector having a cavity forming the housing of said connecting means and at least one location for accommodating a linking element or a locking cylinder,
- said at least one location opening into the cavity forming the housing of said connecting means,
- said connecting means comprising, in its lower part, a spherical shaped part for allowing the connecting means to be positioned freely in at least one of the connector or the linking element having a cavity of complementary shape and when the connecting means are positioned in the cavity of complementary shape of the connector or the linking element, for allowing the connector and the linking element to rotate around the connecting means in two axes perpendicular to the bone anchor means and in an axis identical to that of the bone anchor means,
- said linking element or locking cylinder being in direct contact with and pressing against said spherical shaped part of said connecting means, and
- said spherical shape part forming an end stop for longitudinal positioning with said at least one of the connector and the linking element.

20. A connecting assembly for spinal osteosynthesis comprising:
- a bone anchor means having a connecting zone which collaborates with a connecting means,
- said bone anchor means having an external thread which engages a threaded portion of said connecting means,
- a connector having a cavity forming the housing of said connecting means and at least one location for accommodating a linking element or a locking cylinder,
- said at least one location opening into the cavity forming the housing of said connecting means,
- said connecting means comprising, in its lower part, a spherical shape part for allowing the connecting means to be positioned freely in at least one of the connector or the linking element having a cavity of complementary shape and, when the connecting means are positioned in the cavity of complementary shape of the connector or the linking element, for allowing the connector and the linking element to rotate around the connecting means in three axes,
- said spherical shape part forming an end stop for longitudinal positioning with said at least one of the connector and the linking element,
- said connector comprising a locking location which opens into the cavity forming the housing of said connecting means and into the location accommodating the linking element or the locking cylinder, and
- said connecting assembly comprising a locking system which can be introduced into said locking location to lock said connecting assembly by pressing said locking system against said linking element so that said linking element presses against said spherical shape part of said connecting means.

* * * * *